(12) United States Patent
Limaye

(10) Patent No.: US 12,291,462 B2
(45) Date of Patent: May 6, 2025

(54) MEDICAL TUBING HAVING DIFFERING COLOR STATES

(71) Applicant: CareFusion 303, Inc., San Diego, CA (US)

(72) Inventor: Amit Uday Limaye, San Diego, CA (US)

(73) Assignee: CareFusion 303, Inc., San Diego, CA (US)

( * ) Notice: Subject to any disclaimer, the term of this patent is extended or adjusted under 35 U.S.C. 154(b) by 0 days.

(21) Appl. No.: 17/856,762

(22) Filed: Jul. 1, 2022

(65) Prior Publication Data

US 2024/0002249 A1  Jan. 4, 2024

(51) Int. Cl.
  *C01G 37/00* (2006.01)
  *A61M 39/08* (2006.01)

(52) U.S. Cl.
  CPC ........... *C01G 37/006* (2013.01); *A61M 39/08* (2013.01)

(58) Field of Classification Search
  CPC .................................................. A61M 39/08
  See application file for complete search history.

(56) References Cited

U.S. PATENT DOCUMENTS

| | | | | |
|---|---|---|---|---|
| 5,422,018 | A * | 6/1995 | Saunders | B01D 21/20 422/918 |
| 5,806,528 | A * | 9/1998 | Magliochetti | G01K 13/02 215/11.2 |
| 6,511,456 | B1 | 1/2003 | Salinas et al. | |
| 10,806,811 | B2 | 10/2020 | Burapachaisri et al. | |
| 2003/0017073 | A1 | 1/2003 | Eckhardt et al. | |
| 2008/0107564 | A1 | 5/2008 | Sternberg et al. | |
| 2015/0343102 | A1 * | 12/2015 | Romo | A61L 2/10 436/1 |
| 2019/0064241 | A1 * | 2/2019 | Moulton | G01K 3/04 |

FOREIGN PATENT DOCUMENTS

| | | | | |
|---|---|---|---|---|
| EP | 2979725 | A1 * | 2/2016 | A61L 29/06 |
| JP | 2005171038 | | * 6/2005 | |

OTHER PUBLICATIONS

Nurse.com, "Mothers of invention: California RNs debut color-tinted IV lines," dated Jun. 18, 2022, 5 pages, https://www.nurse.com/blog/mothers-of-invention-california-rns-debut-color-tinted-iv-lines/.
Americos, "Photochromic pigments or colours—change from clear to the target colour when exposed to sunlight or UV light", 3 pages, https://colourchangingpigment.com/photochromic-pigments/, retrieved from https://web.archive.org/web/20230426010701/https://colourchangingpigment.com/photochromic-pigments/.
International Search Report and Written Opinion for Application No. PCT/US2023/026013, dated Sep. 7, 2023, 13 pages.
Written Opinion from the International Preliminary Examining Authority for Application No. PCT/US2023/026013, dated Jan. 9, 2024, 6 pages.
International Preliminary Report on Patentability from the International Preliminary Examining Authority for Application No. PCT/US2023/026013, dated Sep. 2, 2024, 14 pages.

* cited by examiner

*Primary Examiner* — Michael C Miggins
(74) *Attorney, Agent, or Firm* — Morgan, Lewis & Bockius LLP

(57) ABSTRACT

Medical tubing can have a chromic material such that the medical tubing is configured to transition from a first state of color to a different, second state of color by application of a stimulus to the medical tubing.

19 Claims, 1 Drawing Sheet

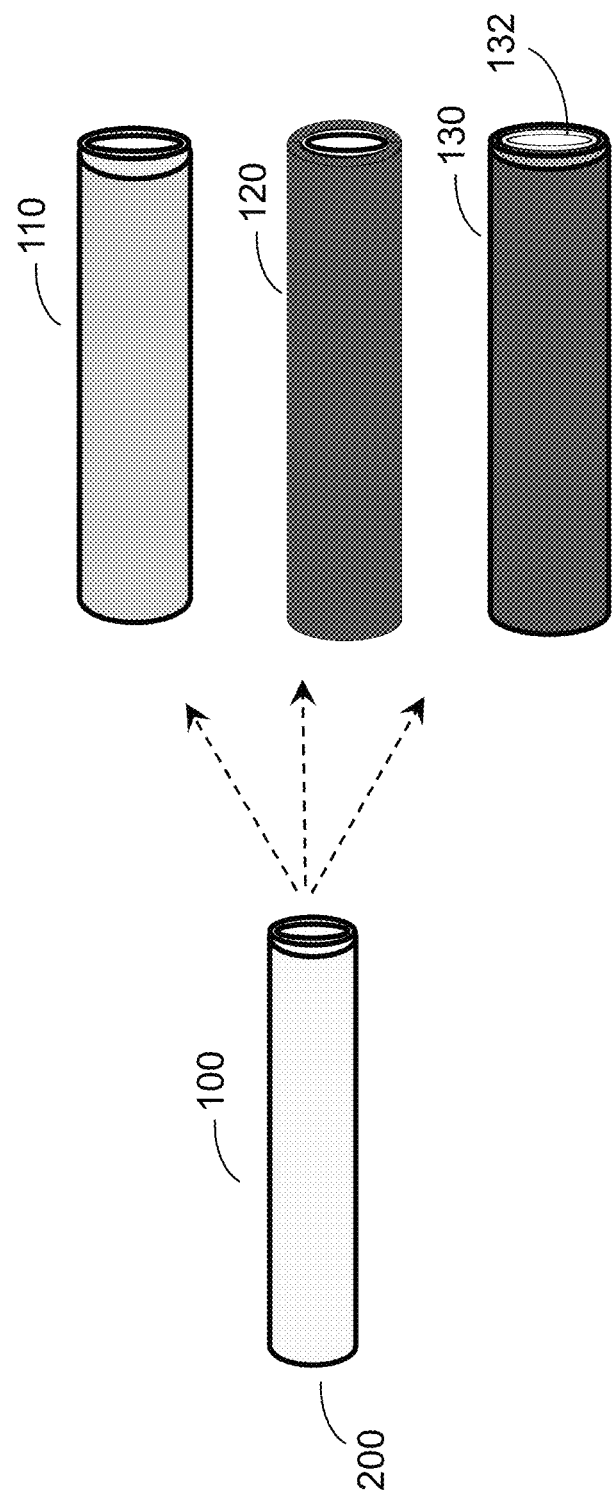

MEDICAL TUBING HAVING DIFFERING COLOR STATES

TECHNICAL FIELD

The present disclosure generally relates to tubing and, in particular, to medical tubing that can have a color and useful for administration of medical fluid by infusion.

BACKGROUND

Plastic tubing is extensively used in the medical field, particularly for patient analysis and treatment procedures. Such tubing is typically transparent and colorless so that the practitioner can observe the state of fluid transport through the tubing. Other than its container, infusion fluid is principally in contact with medical tubing, which has a relatively large surface area, and when the tubing is transparent and colorless, the infusion fluid is exposed to a relatively high amount of ambient light when passing through the tubing.

However, infusion fluid can include light sensitive active ingredients (e.g., light sensitive drugs), which necessitate certain precautions for their administration. This is important since any exposure of the infusion fluid, particularly to ambient light is highest when it is passing through the infusion tubing. To mitigate potential degradation or deactivation of light sensitive drugs, practitioners resort to using amber colored or tinted tubing. Also it is seen in practice that hospitals are sometimes either unable or unwilling to stock two different types of tubing (having variety of connections etc.) and will instead resort to covering their tubing using colored sleeves or opaque coverings to protect infusion fluid including light sensitive drugs.

SUMMARY

In view of the challenges described above, a continuing need exists for medical tubing that can address differing demands of medical applications. Aspects of the subject technology relate to medical tubing having a chromic material, or multiple chromic materials, such that the medical tubing is configured to transition from a first state of color to one or more other states of color that is/are different from the first state of color and are different from other states of color, e.g., a second state of color (that is different from the first state of color), by application of a stimulus to the medical tubing, e.g., heat or light. The medical tubing can also be configured reverse the transition of the states of color, e.g., to transition from the second state of color back to the first state of color, by application or removal of a stimulus to the medical tubing. The one or more chromic materials can be coated on the medical tubing or included in one of an outer layer or an intermediate layer of a multilayer medical tubing. The one or more chromic materials can alternatively, or in addition, be included in a liner on an outer surface layer of the medical tubing.

Advantages of the subject technology include improved workflow, reduction of complexity, etc. by coding medical tubing according to the present disclosure with one more different color states for administration of different medicinal fluids. For example in an aspect of the present disclosure, a method of using medical tubing of the present disclosure includes administering a first medicinal fluid in a first medical tubing wherein the state of color of the first medical tubing was formed by applying a stimulus to the first medical tubing to transition the first medical tubing from a first state of color of the first medical tubing to a different, second state of color. Additional tubing can be used to administer different medicinal fluids.

Another example includes using more than one medical tubing for administration of more than one medicinal fluid can include: administering a first medicinal fluid in a first medical tubing and administering a second medicinal fluid in a second medical tubing; wherein the second medical tubing has a state of color and the first medical tubing has a state of color that is different than the state of color of the second medical tubing, and wherein the state of color of the first medical tubing was formed by applying a stimulus to the first medical tubing to transition the first medical tubing from a first state of color of the first medical tubing to a different, second state of color of the first medical tubing. Other methods of using more than one medical tubing for administration of more than one medicinal fluid can include: applying a stimulus to a first medical tubing to transition the first medical tubing from a first state of color of the first medical tubing to a different, second state of color of the first medical tubing; applying a stimulus to a second medical tubing to transition the second medical tubing from a first state of color of the second medical tubing to a different, second state of color of the second medical tubing. For this method, the second state of color of the first medical tubing is different than the second state of color of the second medical tubing. The method can further include administering a first medicinal fluid in the first medical tubing and administering a second medicinal fluid in the second medical tubing.

Embodiments include one or more of the following features individually or combined. For example, the one or more chromic materials can include a thermochromic material and the stimulus comprises heat. Such chromic materials can include one or more of a Leuco dye, thermochromic inks, poly-3-hexylthiophene, polyacetylenes vanadium dioxide, $Ag_2HgI_4$, or $CoCl_2$, etc. Other examples include wherein the chromic material comprises a photochromic material and the stimulus comprises light. Such chromic materials can include one or more of a an organometallic complexe, spiropyran, spirooxazine, diarylethene, azobenzene, photochromic quinone, inorganic photochromic, salicylidene-aniline, 2-methylbenzo[1,3]oxazine, 4-methoxyazobenzene, or yttrium oxyhydride. In other embodiments, the medical tubing is composed of one or more of a polyolefin, polyvinyl chloride (PVC), a polystyrene (PS), a styrenic based thermoplastic elastomer (TPE) or a styrenic based thermoplastic olefin (TPO), or a acrylonitrile-butadiene-styrene (ABS).

Additional advantages of the subject technology will become readily apparent to those skilled in this art from the following detailed description, wherein only certain aspects of the subject technology are shown and described, simply by way of illustration. As will be realized, the subject technology is capable of other and different configurations, and its several details are capable of modifications in various other respects, all without departing from the subject technology. Accordingly, the drawings and description are to be regarded as illustrative in nature, and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings:

FIG. 1 illustrates medical tubing in accordance with aspects of the present disclosure.

DETAILED DESCRIPTION

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions are provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

Aspects of the subject technology relate to medical devices that can come in contact with infusion fluid that include light sensitive ingredients as well as medicinal fluids that do not contain such ingredients. Medical treatments often include the infusion of a medical fluid (e.g., a saline solution or a liquid medication) to patients using an intravenous (IV) catheter that is connected though an arrangement of flexible tubing and fittings, commonly referred to as an "IV set," to a source of fluid, for example, an IV bag. Such medical tubing and other devices of the infusion assembly can be made from polymeric materials, such as polyvinyl chloride, polyolefins and/or thermoplastic elastomers.

Aspects of the subject technology relate to tubing and, in particular, to medical tubing for administration of medical fluid by infusion. The medical tubing can be a monolayer tube or multilayer tube. Various aspects of the present disclosure provide a medical grade tubing having a chromic material such that the medical tubing is configured to transition from a first state of color to a different, second state of color (that is different from the first state of color) by application of a stimulus, e.g., heat or light. The medical tubing can also be configured to transition from the second state of color back to the first state of color by application or removal of a stimulus to the medical tubing.

The chromic material can be coated on an outer surface of the medical tubing such as by any coating techniques including printing or painting. In combination thereof, or as an alternative, the chromic material can be included within an outer layer or intermediate layer of a multilayer medical tubing such as by incorporated the chromic material into a carrier resin of an outer and/or intermediate layer in forming a multilayered medical tube. The chromic material can alternatively, or in addition, be included in a liner on an outer surface of the medical tubing.

The aforementioned configurations with the chromic material incorporated into an outer layer or intermediate layer or liner are advantageous since an inner layer of the multilayer tubing, or the tubing itself with an outer liner, can serve as a barrier to prevent potential migration of the chromic material leaching into medical fluid flowing through the tubing.

The chromic material can cause the tubing to change from a first color state to a different, second color state. In some embodiments, the transition from the first color state is generally not reversible and in other embodiments, the transition can be reversible, i.e., the second state of color can be transitioned back to the first state of color from the second state of color by application or removal of a stimulus to the medical tubing.

The first colored state can be an absence of a color or a very light color such that the first colored state imparts a transparent medical tube having little to no color, i.e., a colorless transparent tubing. Upon application of an external stimulus, the chromic material is configured to cause the medical tubing to transition to a different, second color state. Such a second color state can be a dark color such as red, maroon, brown, dark grey, green, blue etc. or a tint or yellow. The tubing can be transparent or translucent or exclude a substantial amount (more than 50%) of visible light in the second color state. In some embodiments, the re-application of the stimulus or another stimulus, can cause the medical tubing to revert back to the first color state. This is obtained by utilizing color switching agents such as pigments, or dyes which change color following the application of a specific stimulus such as heat (thermochromic) or illumination of a certain wavelength (Photochromic).

The chromic material can include one or more thermochromic materials that undergo thermochromism, i.e., a color change caused by a temperature change. Such thermochromic materials are widely used in color changing commodity items such as ceramicware, clothing etc. Often the color reverses upon removal of the thermal stimulus, but materials that enable a one-way color change can be used in the present disclosure. Non-limiting examples include one or more of Leuco dyes, thermochromic inks etc. Specific examples of organic thermochromic materials include Poly-3-hexylthiophene and Polyacetylenes which undergo color transitions around 70° C., while inorganic vanadium dioxide, $Ag_2HgI_4$, and $CoCl_2$ which exhibit color transition in the range of 50° C. to 75° C. are examples of inorganic materials. For this embodiment, tubing types can be easily switched to their colored version using readily available hospital accessories such as blanket warmers, IV bag warmers etc.

The loading of the chromic material on or into medical tubing or a layer or liner thereof depends on the nature of the chromic material (organic vs. inorganic) and intensity of desired color change. For inorganic chromic materials, typically a master batch loading of up to 5% in the polymer to be extruded is expected, with a range of 25% to 50% by weight of the inorganic material within the master batch. Similarly for an organic chromic material the final tubing may be expected to have a 100 ppm to 1,000 ppm of the chromic material.

In addition, or as an alternative, the chromic material can include one or more photochromic materials that undergo photochromism, i.e., a color change caused by the application of a certain wavelength of light. Such photochromic materials include a wide variety of alternatives since multiple different dyes and pigments resulting in different colored tints can be easily achieved. Non-limiting examples include one or more of organometallic complexes, Spiropyrans, spirooxazines, Diarylethenes, Azobenzenes, Photochromic quinones, Inorganic photochromics and Photochromic coordination compounds. While some of the above are reversible photochromic compounds, the duration of reversal may be adequate or can be modulated to provide protection for the desired duration. Specific examples of organic photochromic materials include salicylidene-aniline, 2-methylbenzo[1,3]oxazine, and 4-methoxyazobenzene, which undergo color transformation at wavelengths of 365 nm, 591 nm, and 365 nm respectively. Similarly, Yttrium oxyhydride, an inorganic material exhibits color change when exposed to broad spectrum solar radiation.

An advantage of medical tubing with more than one chromic material is that the tubing can be configured to change from a first color state to one or more different, second color states, e.g., a second state of color, a third state of color, a fourth state of color, etc. wherein each first, second, third, and fourth, etc., state of color has a different, distinct state of color from any other state of color. As an example, medical tubing of the present disclosure can include a first chromic material (chromic material A) and a second chromic material (chromic material B) on or within the tubing or in one or more layers. Alternatively, different chromic materials (chromic material A) can be included in one layer of a multilayer medical tubing and another different chromic material (chromic material B) can be included in a second layer of a multilayer medical tubing. Alternatively, or in addition to the above, multiple chromic material can be included in one or more liners on an outer surface of the medical tubing wherein the different chromic materials can be in the same liner or in different liners on the medical tubing. Hence, in an aspect of the present disclosure, medical tubing can include more than one chromic materials (Chromic materials A and B) and configured to transition from a first state of color to a different, second state of color or to a different, third state of color, or to a different, fourth state of color, etc. by application of a stimulus to the medical tubing. The medical tubing can further be configured to reverse each of the transitions by use of appropriate chromic materials and application or removal of stimulus.

The second, thirds, fourth, et. state of color can be selected among different colors, e.g., yellow, green, blue, red, maroon, brown, dark grey, etc. A selection of medical tubing that can change to different second, third, etc. state of colors or a selection of a first and second and third medical tubing that are configured to change to a second state of color wherein each second stat of color of the second, third, etc. medical tubing is different from each other would allow the practitioner to readily color code the medical tubing into different colored tubing to code the tubing. Color coding medical tubing for administration of different medicinal fluids can assist in identifying which tubing is used for which administration of which medicinal fluid when multiple medical tubing are used for administration of different medicinal fluids to a single patient. For example, a method of using more than one medical tubing for administration of more than one medicinal fluid can include: administering a first medicinal fluid in a first medical tubing and administering a second medicinal fluid in a second medical tubing. Either or both of the first and second medical tubing can undergo a color change by application of a stimulus to the tubing to differentiate the colors of the tubing. For example, the second medical tubing can have a native state of color and the first medical tubing can have a state of color that is different than the state of color of the second medical tubing. The state of color of the first medical tubing can be formed by applying a stimulus to the first medical tubing to transition the first medical tubing from a first state of color of the first medical tubing to a different, second state of color of the first medical tubing. In other aspects, a method of using more than one medical tubing for administration of more than one medicinal fluid can include: applying a stimulus to a first medical tubing to transition the first medical tubing from a first state of color of the first medical tubing to a different, second state of color of the first medical tubing; applying a stimulus to a second medical tubing to transition the second medical tubing from a first state of color of the second medical tubing to a different, second state of color of the second medical tubing. For this method, the second state of color of the first medical tubing is different than the second state of color of the second medical tubing. The method can further include administering a first medicinal fluid in the first medical tubing and administering a second medicinal fluid in the second medical tubing. The medicinal fluids can be different and thus in different colored tubing, which can facilitate identification of various different medicinal fluids to a patient.

In an aspect of the subject technology, the medical tubing of the present disclosure can be changed to a second color state to create a light protection tubing (to protect drugs), or just colored tubing to enable reduction in workflow confusion/complexity. The thermochromic agents can be applied onto the tubing or compounded into the material as it is extruded. The medical tubing and layers thereof of the present disclosure can be composed of one or more of a polyvinyl chloride (PVC), a polyolefin such as a polyethylene (PE), a polypropylene (PP), etc., a polystyrene (PS), a styrenic based thermoplastic elastomer (TPE) or a styrenic based thermoplastic olefin (TPO), a acrylonitrile-butadiene-styrene (ABS).

Activation and switching can be achieved using a light source of the correct wavelength that is supplied as a separate durable accessory or by application of heat.

FIG. 1 illustrates medical tubing in accordance with aspects of the present disclosure. As shown in the FIGURE, tubing, e.g., medical tubing 100 for fluid transport therethrough 200, can include chromic material on an outer surface of the tubing 110. The medical tubing can be comprised of PVC or a thermoplastic elastomer, for example. The chromic material can be incorporated on the outer surface by any coating technique including painting, printing, etc.

As an alternative, or in addition to an outer coating, medical tubing 100 can include chromic material as an liner 120 of the tubing 100. In such an embodiment, a conventional medical tubing, e.g., one comprised of PVC or a thermoplastic elastomer (TPE) can have a lining on the outside surface of the tubing with the chromic material included in or on the lining. Such a liner or outer layer can comprise a polyolefin, e.g., a polyethylene (PE) or similar polyolefin, that includes the chromic material in the polyolefin or a layer thereof.

As an alternative, or in addition to either or both of the foregoing, the medical tubing can include chromic material within an outer layer 130. In such an embodiment, the medical tubing 100 has at least an additional layer which does not include chromic material, e.g., an inner layer 132. The outer layer can be comprised of a PVC or TPE and the inner layer can include a polyethylene (PE) or similar polyolefin, for example.

An advantage of using a liner or outer layer having the chromic material and an inner layer without the chromic material is that the tubing with the liner or outer layer can be configured to be impervious to the transport of the chromic material from or through the liner or outer layer to fluid transported through the tubing. That is, the tubing with the liner or tubing with an inner layer without the chromic material can be impervious to transport of the chromic material from an outer surface to an inner surface where fluid is transported through the tubing.

In some embodiments, the outer layer 130 and the inner layer 132 can each be formed from the same base material such as, for example, from the same polymeric resin material. The layers can be co-extruded such that outer layer directly contacts the inner layer, directly along the tubing length without a tie layer between the outer and inner layers or with a tie layer between the outer and inner layers.

For example, in some embodiments the inner and outer layers can each have a thickness ranging from 0.2 mm to 0.8 mm, such as from 0.4 mm to 0.6 mm. In some embodiments, tubing of the present discloser can have an inner diameter for flow of fluid therethrough ranging from about 0.1 mm to about 6 mm, e.g., from about 0.5 mm, 1 mm, 1.5 mm, etc. to about 6 mm, e.g., from 2 mm to 4 mm.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, operations or processes disclosed is an illustration of exemplary approaches. Based upon design preferences, it is understood that the specific order or hierarchy of steps, operations or processes may be rearranged. Some of the steps, operations or processes may be performed simultaneously. Some or all of the steps, operations, or processes may be performed automatically, without the intervention of a user. The accompanying method claims, if any, present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112 (f) unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but are to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. Medical tubing, for fluid transport therethrough, having a chromic material, wherein the medical tubing is configured to transition from a first state of color to a different, second state of color by application of a stimulus to the medical tubing,
wherein the medical tubing comprises an inner layer without the chromic material and an outer layer comprising the chromic material, the inner layer and the outer layer comprising a same base material,
wherein the tubing is colored transparent or colored translucent in one or both of the first state of color and the second state of color.

2. The medical tubing of claim 1, wherein the chromic material is included on a surface of the medical tubing or within an outer layer of the medical tubing.

3. The medical tubing of claim 1, wherein the medical tubing includes an outer lining that includes the chromic material.

4. The medical tubing of claim 1, wherein the medical tubing includes an outer layer and an inner layer wherein the outer layer includes the chromic material.

5. The medical tubing of claim 1, wherein the medical tubing comprises more than one chromic materials and is configured to transition from a first state of color to a different, second state of color, or to a different, third state of color by application of a stimulus to the medical tubing.

6. The medical tubing of claim 1, wherein the medical tubing is composed of one or more of a polyvinyl chloride (PVC), a polyolefin, a polystyrene (PS), a styrenic based thermoplastic elastomer (TPE) or a styrenic based thermoplastic olefin (TPO), or a acrylonitrile-butadiene-styrene (ABS).

7. The medical tubing of claim 1, wherein the first state of color is a colorless transparent tubing.

8. The medical tubing of claim 1, wherein the second state of color is a red, maroon, brown, dark grey, yellow, blue, or green.

9. The medical tubing of claim 1, wherein the medical tubing includes an inner layer that is impervious to transport of the chromic material through the inner layer to fluid transported through the medical tubing.

10. The medical tubing of claim 9, wherein the inner layer comprises a polyolefin.

11. The medical tubing of claim 1, wherein the chromic material comprises a thermochromic material and the stimulus comprises heat.

12. The medical tubing of claim 11, wherein the thermochromic material comprises one or more of a Leuco dye, thermochromic ink, poly-3-hexylthiophene, polyacetylene vanadium dioxide, $Ag_2HgI_4$, or $CoCl_2$.

13. The medical tubing of claim 1, wherein the chromic material comprises a photochromic material and the stimulus comprises light.

14. The medical tubing of claim 13, wherein the photochromic material comprises one or more of an organometallic complex, spiropyran, spirooxazine, diarylethene, azobenzene, photochromic quinone, inorganic photochromic, salicylidene-aniline, 2-methylbenzo [1,3] oxazine, 4-methoxyazobenzene, or yttrium oxyhydride.

15. Medical tubing, for fluid transport therethrough, having a chromic material, wherein the medical tubing is configured to transition from a first state of color to a different, second state of color by application of a stimulus to the medical tubing and wherein the medical tubing is configured to transition from the second state of color back to the first state of color by application or removal of a stimulus to the medical tubing, wherein the medical tubing comprises an inner layer without the chromic material and an outer layer comprising the chromic material, the inner layer and the outer layer comprising a same base material, wherein the tubing is colored transparent or colored translucent in both of the first state of color and the second state of color.

16. The medical tubing of claim 15, wherein the chromic material comprises a thermochromic material and the stimulus comprises heat.

17. The medical tubing of claim 16, wherein the thermochromic material comprises one or more of a Leuco dye, thermochromic ink, poly-3-hexylthiophene, polyacetylene vanadium dioxide, $Ag_2HgI_4$, or $CoCl_2$.

18. The medical tubing of claim 15, wherein the chromic material comprises a photochromic material and the stimulus comprises light.

19. The medical tubing of claim 18, wherein the photochromic material comprises one or more of an organometallic complex, spiropyran, spirooxazine, diarylethene, azobenzene, photochromic quinone, inorganic photochromic, salicylidene-aniline, 2-methylbenzo [1,3] oxazine, 4-methoxyazobenzene, or yttrium oxyhydride.

* * * * *